(12) United States Patent
Rapkin et al.

(10) Patent No.: US 7,364,695 B2
(45) Date of Patent: Apr. 29, 2008

(54) HIGH VOID VOLUME AND/OR HIGH LIQUID IMBIBING BASED APPARATUS

(75) Inventors: Myron C. Rapkin, Indianapolis, IN (US); Claude R. Gunter, Indianapolis, IN (US)

(73) Assignee: Taylor Technologies, Inc., Sparks, MD (US)

( * ) Notice: Subject to any disclaimer, the term of this patent is extended or adjusted under 35 U.S.C. 154(b) by 836 days.

(21) Appl. No.: 10/303,207

(22) Filed: Nov. 25, 2002

(65) Prior Publication Data

US 2003/0175152 A1 Sep. 18, 2003

Related U.S. Application Data

(60) Provisional application No. 60/339,741, filed on Dec. 12, 2001.

(51) Int. Cl.
*G01N 31/22* (2006.01)

(52) U.S. Cl. .......................................... 422/56; 422/57
(58) Field of Classification Search ................... 422/56
See application file for complete search history.

(56) References Cited

U.S. PATENT DOCUMENTS

| 4,144,306 | A | * | 3/1979 | Figueras ........................ 422/56 |
| 4,587,102 | A | * | 5/1986 | Nagatomo et al. ............. 422/56 |
| 5,124,266 | A | * | 6/1992 | Coryn et al. ................... 422/56 |
| 5,750,333 | A | * | 5/1998 | Clark ............................ 435/5 |
| 6,074,869 | A | * | 6/2000 | Pall et al. ................. 435/286.5 |
| 6,413,473 | B1 | * | 7/2002 | Bacon ........................... 422/56 |
| 6,602,719 | B1 | * | 8/2003 | Carpenter ..................... 436/518 |

\* cited by examiner

*Primary Examiner*—Jill Warden
*Assistant Examiner*—Natalia Levkovich
(74) *Attorney, Agent, or Firm*—Fulbright & Jaworski L.L.P.

(57) ABSTRACT

The present invention provides test carriers to determine the presence or amount of a given substance in a liquid sample. The present invention also provides apparatus and methods for analyzing liquid samples using these test carriers.

20 Claims, 4 Drawing Sheets

Figure 1 - Percent of Color Range Covered by pH Test Strips

Figure 3 - Range of Colors Developed by Water Hardness Test Strips

Hash marks represent colors developed at 0, 50, 100, and 200 ppm Calcium Hardness. Troy 777 felt strips show an increased color development at the levels tested.

HIGH VOID VOLUME AND/OR HIGH LIQUID IMBIBING BASED APPARATUS

FIELD OF THE INVENTION

The application claims priority from U.S. Provisional Application Ser. No: 60/339,741 filed Dec. 12, 2001.

This invention relates to apparatus and methods, and reagents useful in analyzing liquid samples. More particularly, the invention relates to analyzing liquid samples to determine a given amount of a given substance in the liquid sample. The invention is useful in, e.g., test apparatus which have improved sensitivity and accuracy and in all diagnostic test devices such as those useful in determining if a parameter of a liquid sample is present, the amount of the parameter or analyte, and/or if it requires adjustment, and to what degree.

BACKGROUND AND PRIOR ART

The science of analytical chemistry has, and continues to make progress. The field involves the ability to assay sample materials to determine if a particular substance or substances is present, and if so, the amount of that substance. Frequently, the term "analyte" is used to describe the substance being tested. This term will be used hereafter.

Early examples of the application of analytical chemistry include litmus paper, which changes color in response to acid or base concentration as well as devices such as those incorporating test papers measuring urinary protein. To say that the field has become more sophisticated since then is an understatement.

One area of importance in analytical chemistry is the testing and evaluation of liquid samples. "Liquid sample" as used hereafter refers to materials such as blood, urine and, more particularly for this disclosure, water.

It is desirable and necessary to analyze water for various components. For example, it may be important to determine if a water sample is potable. Further, water samples are used for different purposes. Depending upon the use to which the sample is to be put, one or more parameters, such as pH, total alkalinity, calcium hardness, total hardness, and amount of particular analytes such as total chlorine, free chlorine, combined chlorine, sodium content, etc., may be important. For example, when the water sample is taken from a swimming pool, either or both of combined chlorine and free chlorine may be important. Where the water is to be used for an industrial cooling system, total alkalinity or total hardness may be important. When the water is to be used in the health profession, any number of analytes may be of interest and important. These are some examples of the type of uses for water samples. The skilled artisan will be familiar with many others, which need not be set forth here. Further, the literature on analysis of liquid samples other than water is vast.

Analysis of water samples can be accomplished with any number of different systems. Generally, however, these systems can be divided into "dry chemistry" and "wet chemistry" systems.

In a wet chemistry system, essentially one adds either a liquid testing agent or a dissolvable testing agent to a liquid sample. The testing agent reacts with the analyte of interest, leading to formation of a detectable signal. Preferably, this is the formation of a visible "marker," such as a color or change in color. Again, the artisan will be familiar with other systems such as measurement of light absorption photometers, etc. For purposes of this disclosure, however, the discussion will focus on visible formation and changes in color, rather than systems such as light photometers solely to facilitate understanding.

In these wet chemistry systems, the reacted liquid sample is then compared to some reference standard. Generally, this takes the form of a coded reference linking concentration of the analyte to a particular color or degree of color. A low concentration may be indicated by a very pale pink color, and a high concentration by one which is dark red, and vice versa.

Dry chemistry systems can be used to analyze many of the types of samples that wet chemistry systems are used to analyze. In these dry chemistry systems an apparatus, such as an absorbent pad or a test strip is impregnated with the test system discussed herein. The apparatus is contacted with the liquid sample, removed from it, and signal is "read" by means of the color formed, a coded reference, etc. As with wet chemistry systems, the signal that is generated is linked to a specific amount and/or concentration of an analyte under consideration.

The prior art literature on analytical chemistry is vast. For example, U.S. Pat. No. 4,811,254, to Wu, teaches reagent systems which can be used to detect total available chlorine over a range of from 0 to 5000 ppm. The reagents can be incorporated into a carrier matrix, such as filter paper, to produce a dry chemistry test strip useful in measuring total available chlorine. U.S. Pat. No. 5,710,372, to Becket, teaches test strips which include a plurality of test regions. Each region contains a different amount of a reagent system which reacts with an analyte of interest. A visual display results which permits the user to determine the amount of the analyte in the sample being analyzed. U.S. Pat. No. 5,620,658, to Jaunakais, teaches multicomponent test strips which contain reagents capable of converting undetectable analytes into detectable ones, via ionic change. U.S. Pat. No. 5,529,751, to Gargas, teaches a pH adjustment kit. Once the pH of the sample has been determined, a first reagent is added until the sample indicates that a proper pH has been obtained. The number of drops of the first reagent is then converted to a quantity of a second reagent, which is then used to modify pH of the source of the sample. U.S. Pat. No. 5,491,094, to Ramana, et al., teaches dry reagent test strips for determining free chlorine, using TMB derivatives. U.S. Pat. No. 4,904,605, to O'Brien, et al., teaches test strips which can be used to determine a plurality of different reagents. A dipstick containing a plurality of reagent pads is contacted to sample, signal is formed, and then compared to a reference standard. U.S. Pat. No. 4,481,296, to Halley, teaches compositions that are useful in determining the pH of a halogen containing solution.

The various forms of analytical test strips can be seen via review of, e.g., U.S. Pat. Nos. 5,962,339 and 5,302,346, to Midgley et al and Vogel et al, respectively, who incorporate movable particles into the test strips. U.S. Pat. No. 5,271,895 to M$^c$Croskey and U.S. Pat. No. 5,169,787 to Knappe utilize apparatus which separate materials from sample, while U.S. Pat. No. 6,159,747 to Harttig et al teaches a blister device in the apparatus which, when broken, distributes reagent. Various specific types of assays are also described as being available in dry chemistry apparatus form. U.S. Pat. No. 5,874,944 to Kuo, U.S. Pat. No. 5,468,647 to Skold, and U.S. Pat. No. 5,824,268 to Bernstein are exemplary of immunoassays that can be performed on apparatus of the type described herein. U.S. Pat. No. 5,922,283 to Hsu et al; U.S. Pat. No. 5,709,837 to Mori et al, U.S. Pat. Nos. 6,027,692 and 5,695,494 to Gelen et al; U.S. Pat. No. 5,470,752 to Burd, U.S. Pat. No. 4,806,478 to Stahl and U.S.

Pat. No. 4,966,855 to Deneke et al all discuss specific reagent systems which can be used in dry chemistry test strip form.

Regardless of the type of assay carried out, the test apparatus requires a matrix of some type to which analytical reagents and samples can be applied. Classically, filter paper or other types of paper are used; however, the art has demonstrated that various other materials have been used. Rothe, et al, U.S. Pat. No. 4,604,264, is exemplary of a class of test strips which incorporate reagent containing films. Other U.S. patents, such as U.S. Pat. Nos. 3,897,214 to Lange et al; 3,802,842, also to Lange, et al, and U.S. Pat. No. 4,042,335 to Element describe the use of fleece, felt, or floculent materials, e.g., flocks, in test devices.

The plethora of U.S. patents in this area, coupled with the diverse approaches taken to the construction of the devices exhibits constant attempts to improve the quality and diversity of the devices.

One major issue that faces the manufacturer of any test apparatus is the need to have a device available that provides clear, easy to read signals where the amount of analyte in a sample is very small. Generally, test strips of the type described herein contain reagents which, upon reaction with a particular analyte, generate an observable signal, such as a color. In test strips designed to measure the amount of an analyte present, such as a pH test strip, the signal must be one which provides a distinct color or color change over a range of values, such that the different values can be distinguished from each other easily. A pH test strip that gave the same color whether the pH of a sample was 6.0 or 8.0, e.g., is useless in many applications.

In order to be useful, a test strip used in this situation should be able to delineate between analyte values clearly, accurately, and distinctly.

Another problem with test strips that are used to analyze samples containing vanishingly small amounts of analyte is that the test strips, when contacted to a liquid sample, de facto add reagents to the sample. Such reagents frequently contain materials such as buffers, which impact the analyte of interest.

It has now been found, however, that one can improve the usefulness of test strips and analytical devices markedly if one employs, as the matrix, a material which contains, at a minimum, a void fraction or void volume of at least about 80%, more preferably at least about 85%, more preferably at least about 90%, even more preferably at least about 93%, and most preferably about 93-97%.

"Void volume" or "void fraction" as used herein, are terms known in the art. One way of determining percent void volume is to use the following formula:

$$V = \left[\frac{t - (f/d + m)}{t}\right] \times 100$$

where V is the void volume, t is felt volume, f is the dry weight of the felt, d is the density of the material, and m is felt moisture. Of course, if another material, such as fleece is used, the adjective "felt" will change. A written definition is provided by *The Dictionary of Paper*, (George Banta Company, Menasha, Wis., 1965), incorporated by reference, which defines void fraction as "the ratio of the volume occupied by voids or air spaces to the gross volume of a sheet of paper. It may also be expressed as" unity minus the solid fraction." The definition, while provided for paper, is employed herein for all types of matrices used.

It has also been found that the usefulness of test strips and analytical devices improves markedly if one uses, as the test matrix, absorbent material which, when contacted to liquids, imbibes from about 6 to about 30 times its dry weight in liquid, more preferably from about 6 to about 20 times its dry weight, and even more preferably, from about 8 to about 17 times its dry weight in liquid. This value is referred to as "uptake ratio," defined as the value obtained by dividing the weight of water imbibed by the material, by its dry weight. In one embodiment of the invention, the imbibing property referred to herein and the void volume property referred to supra are shared by the material used for the matrix.

The examples which follow are exemplary of the invention, but should not be seen as being limiting of the general convention as described herein.

DETAILED DESCRIPTION OF PREFERRED EMBODIMENTS

EXAMPLE 1

Figure 1:
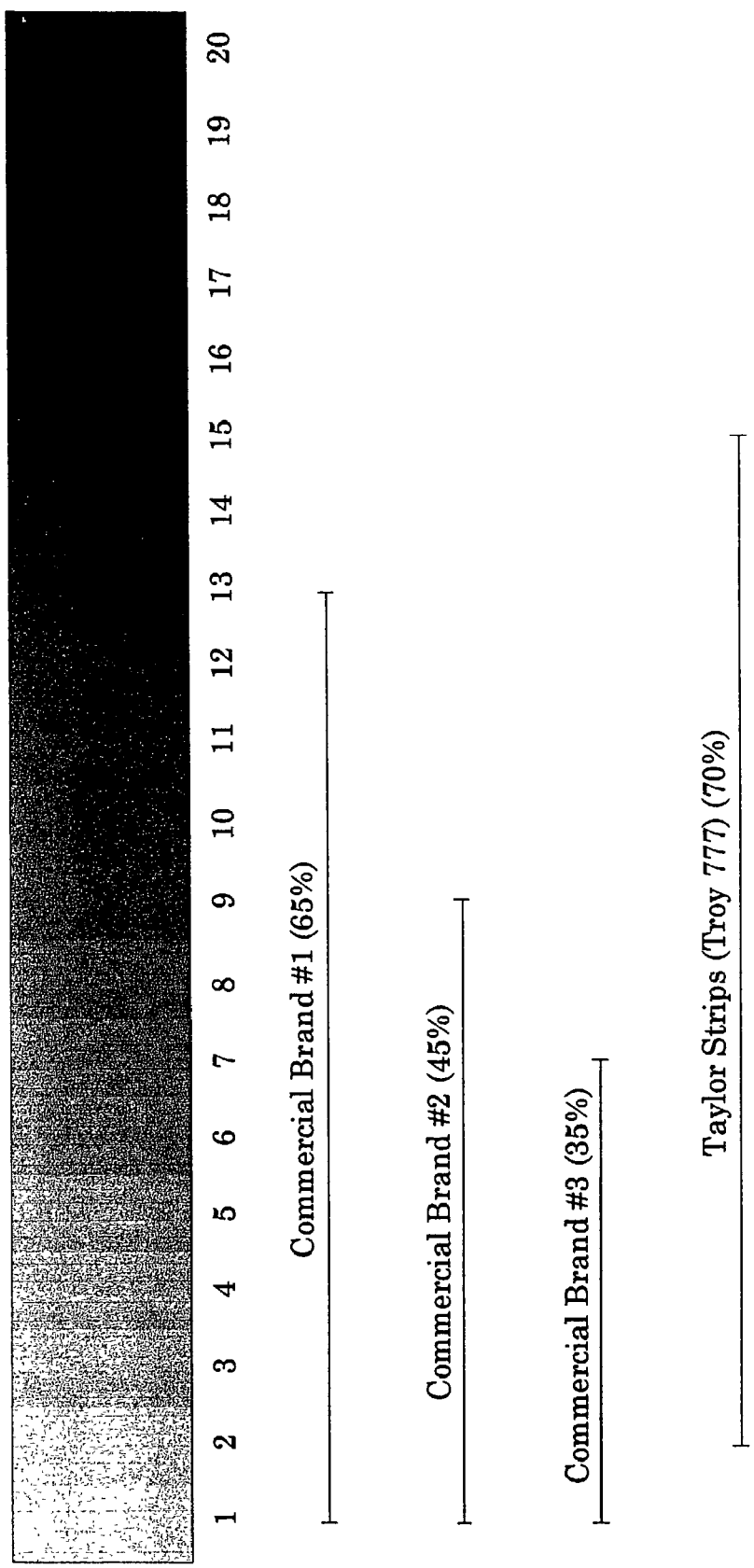
FIG. 1 depicts the percent of color range covered by pH test strips.

Preliminary experiments were carried out to determine the capacity of felt materials for taking up fluids. A composite felt containing material "STD 230TF-1" was obtained from Airformed Composites, Inc. and tested. First, 1 $cm^2$ disks were punched out of the product, using a steel sampling punch. The disks were weighed, placed in water and weighed after a period of time in the water. Ratio of uptake was calculated by dividing the weight of water absorbed by the weight of the dry disk. The results, for three tests, were as follows:

| Test # | 1 | 2 | 3 |
|---|---|---|---|
| Dry Disk Weight | 0.0231 | 0.0230 | 0.0231 |
| Weight After Immersion | 0.3486 | 0.3370 | 0.3683 |
| Weight Absorbed | 0.3255 | 0.3140 | 0.3452 |
| Ratio | 14:1 | 13.6:1 | 14.9:1 |

Similarly, both felt (Troy 777), and filter paper (Whatman 3 MM), were tested in the same way. The results were as follows. All weights are in milligrams.

| Dry | Wet | Uptake | Ratio of uptake to Dry |
|---|---|---|---|
| Troy 777 | | | |
| 287 | 2947 | 2660 | 9.3 |
| 338 | 3268 | 2930 | 8.7 |
| 291 | 2920 | 2629 | 9.0 |
| 326 | 3296 | 2970 | 9.1 |
| 349 | 3112 | 2763 | 7.9 |
| 294 | 2850 | 2556 | 8.7 |

-continued

|                    | Dry   | Wet    | Uptake | Ratio of uptake to Dry |
|--------------------|-------|--------|--------|------------------------|
|                    | 294   | 2885   | 2591   | 8.8                    |
|                    | 339   | 3061   | 2722   | 8.0                    |
|                    | 322   | 3117   | 2795   | 8.7                    |
|                    | 304   | 3112   | 2808   | 9.2                    |
| Mean               | 314.4 | 3056.8 | 2742.4 | 8.7                    |
| Standard Deviation | 23.1  | 154.4  | 138.3  |                        |

Whatman 3 MM (weights in mg)

|                    | Dry   | Wet   | Uptake | Ratio of uptake to Dry |
|--------------------|-------|-------|--------|------------------------|
|                    | 177   | 511   | 334    | 1.9                    |
|                    | 179   | 519   | 340    | 1.9                    |
|                    | 183   | 514   | 331    | 1.8                    |
|                    | 173   | 498   | 325    | 1.9                    |
|                    | 182   | 508   | 326    | 1.8                    |
|                    | 181   | 516   | 335    | 1.9                    |
|                    | 181   | 578   | 397    | 2.2                    |
|                    | 171   | 471   | 800    | 1.8                    |
|                    | 182   | 527   | 345    | 1.9                    |
|                    | 174   | 501   | 327    | 1.9                    |
| Mean               | 178.3 | 514.3 | 336    | 1.9                    |
| Standard Deviation | 4.3   | 27.1  | 24.6   |                        |

The same protocol was followed for a number of different materials. All experiments were run, in triplicate, and the values given below are the average values obtained.

| MATERIAL | TYPE | UPTAKE |
|---|---|---|
| Mead 74401 | Paper | 4.5 |
| S&S 740E | Paper | 3.9 |
| Ahlstrom 204 | Paper | 3.5 |
| Ahlstrom 205 | Paper | 4.5 |
| Ahlstrom 222 | Paper | 3.2 |
| Whatman CCP500 | Paper | 3.3 |
| Aetna PE9-125 | Felt | 12.5 |
| Buffalo Rayon | Felt | 17.1 |
| Felters A5/000-100-X | Felt | 12.5 |
| Troy 1-1915 | Felt | 8.8 |
| Foss 4AD 745 | Felt | 17.8 |
| Foss 1AA680 | Felt | 12.8 |
| Airformed Composites STD-230 TF-1 | (see below) | 23.8 |

The Airformed Composites material is defined by its manufacturer as "superabsorbent fibers" which contain a polyacrylate base with wood pulp. It is referred to as a superabsorbent polymeric gel.

EXAMPLE 2

Experiments were then carried out to determine if a felt material would imbibe indicator solution, and give accurate readings when tested.

Felt samples were obtained from a commercial supplier (Aetna), cut to appropriate size pieces, and allowed to soak up as much indicator solution as possible. The indicator solution was 0.05% phenol red, in distilled water. Excess solution was removed by pressing between paper towels. The samples were dried at 60° C. for 10 minutes. Prior to drying, the materials were weighed. Before dipping in the solution, the matrix tested weighed 0.121 g, and after soaking, 2.808 g. Hence, it absorbed 23.2 times its weight of liquid.

After the matrix was dried, test strips were prepared by cutting to ⅛" wide strips and laminating to plastic handles, and then tested by dipping into solutions with pH values of 6.8, 7.6 and 8.2. All pH solutions had a total alkalinity of 90 ppm. The strips were compared to a commercially available test strip.

The felt strips were found to give results either equal to or better than the commercial products in terms of sensitivity.

An additional set of experiments were carried out using a 0.05% m-cresol purple indicator. The results were compared to commercially available products which used a paper matrix.

The felt materials of the invention showed slight differentiation in signal at pHs 6.0 and 7.6, and good differentiation between 7.6 and 8.2.

EXAMPLE 3

In these experiments, two felt materials, "Troy 1915" and "Troy 777" were tested. An indicator solution made by combining 5 ml of 0.05% phenol red, and 5 ml of 0.05% m-cresol purple was used. The matrices were tested as described in example 2, and compared to commercially available, ETS strips. The differentiation between various pHs was better with the felt materials than the ETS strip.

The indicator solution was then reformulated, as 9 ml of 0.025% phenol red mixed with 4.5 ml of 0.1% pluronic L64 (surfactant), and tested. The results were even better, with good differentiation between pH levels, and some leaching.

Finally, an indicator solution was prepared using 0.1 g of 5% Klucel EEF (polymer), 3 ml distilled water, 3 ml 0.025% phenol red, 3 ml of 0.025% m-cresol, and tested. The addition of the Klucel seemed to reduce the leeching out of indicator without compromising the differentiation at different pH levels.

EXAMPLE 4

Test strips made from felt were tested to demonstrate that they were able to present a broader range of values than commercially available test strips. An impregnating solution was prepared as follows:

| Component | Amount |
|---|---|
| Distilled Water | 100 ml |
| Phenol Red, Sodium Salt | 46.6 mg |
| 5.0% Pluronic L64 (surfactant) in methanol | 1.86 ml |
| 5.0% Zonyl FSN (surfactant) in methanol | 1.86 ml |

This solution was used to prepare test strips designed to measure pH. 2"×6" pieces of Troy 777 felt were impregnated with the solution by allowing the pieces to imbibe as much solution as they could. Excess solution was removed by blotting between paper towels, and the impregnated felt was dried in a horizontal position at 70° C. for 20 minutes. Test strips measuring 5 mm×5 mm were constructed and evaluated against commercially available state-of-the-art test strips, using solutions at varying pH values ranging from 6.4 to 8.4.

The results of the evaluation, given in FIG. 1, show conclusively test strips made with the Troy 777 felt produced a broader range of colors than commercially available pH strips. Test strips made with the Troy 777 felt also gave more intense colors that were easier to read.

EXAMPLE 5

The pH of the final solution, below, was adjusted from 4.6 to 3.8 with 0.1N HCl. 2"×6" pieces of Troy 777 felt were impregnated with the solution, excess liquid was removed by blotting between paper towels and dried in horizontal position at 70° C. for 20 minutes. Test strips were constructed and evaluated as above, and compared to commercially available, ETS pH test strips.

| Distilled Water | 100 ml |
| Phenol Red, Sodium Salt | 46.6 mg |
| 5.0% Pluronic L64 in MeOH (Surfactant) | 1.86 ml |
| 5.0% Zonyl FSN 100 in MeOH (Surfactant) | 1.86 ml |
| 5.0% Benzalkonium chloride in water | 1.24 ml |

| Tap Water Solution pH | Color Developed With Troy 777 Test Strips | Color Developed With Commercially Available ETS pH Test strips |
| --- | --- | --- |
| 6.4 | Dark Yellow | Orange |
| 6.8 | Dark Yellow-Orange | Orange-Red |
| 7.2 | Dark Orange | Darker Orange-Red |
| 7.5 | Dark Orange-Red | Red-Orange |
| 7.8 | Dark Red | Reddish Orange |
| 8.4 | Darker Reddish Purple | Slightly Darker Reddish Orange |

As can be seen from the results in the Table, the test strips made with the Troy 777 felt gave much expanded color transition in the samples than the commercially available product. Further, the test strips containing the formulation gave more uniform distribution of color throughout the test carrier, and more intense, brighter colors than other formulations. Benzalkonium chloride, when combined with an indicator molecule or system, is believed to facilitate the superior properties exhibited therein.

The indicator composition described herein is in fact exemplary of another feature of the invention, which is compositions which comprise a sulfonphthalein indicator, such as but not being limited to, phenol red, m-cresol purple, or any other such indicator, as well as a cationic surfactant, for example, benzalkonium chloride. There are many examples of both sulfonphthalein indicators and cationic surfactants which will be familiar to the skilled artisan, and need not be reiterated here. The compositions may be in liquid form, dry form such as a powder, or in a form wherein they are impregnated onto test carriers such as, but not limited to, the carriers of this invention. Also a part of the invention are "do it yourself" modules, such as reagent kits where separate portions of the components are provided in a container means, so that the artisan of ordinary skill can admix the materials at such time as it is desirable to do so.

EXAMPLE 6

Test strips were made using the dip solution below and evaluated using another felt (Cushionaire felt matrix, from Central Shippee). All steps were carried out as described in the preceding examples.

| Dip Solution | |
| --- | --- |
| 0.025% Phenol Red, Sodium Salt in D.I. water | 50 ml |
| 5.0% Pluronic L64 in MeOH (Surfactant) | 1.0 ml |
| 5.0% Zonyl FSN 100 in MeOH (Surfactant) | 1.0 ml |
| 1.0% Viscarin GP 209 in D.I. water (polymer) | 1.0 ml |

| Tap Water Solution pH | Color Developed With Cushionaire Test Strips | Color Developed With ETS pH Test strips |
| --- | --- | --- |
| 6.4 | Yellow-Orange | Orange |
| 6.8 | Dark Yellow-Orange | Orange-Red |
| 7.2 | Orange | Darker Orange-Red |
| 7.5 | Orange-Red | Red-Orange |
| 7.8 | Red | Reddish Orange |
| 8.4 | Darker Red | Slightly Darker Reddish Orange |

As can be seen from the results in the table, the test strips made with the Cushionaire felt matrix gave a much expanded color transition in the tap water than the commercially available test strips.

EXAMPLE 7

Additional pH test strips were constructed. A reagent dip solution was prepared according to the table below.

| Dip Solution | |
| --- | --- |
| 0.025% Phenol Red, Sodium Salt in D.I. water | 50 ml |
| 1.0% Viscarin GP 209 | 1.0 ml |
| 5.0% Pluronic L64 in MeOH | 0.5 ml |
| 5.0% Zonyl FSN 100 in MeOH | 0.5 ml |

Three different types of felt, Troy 777, Troy 134 and Troy 143 were compared. 2"×6" pieces of felt were impregnated with the above solution, the excess liquid was removed by blotting between paper towels and dried in the horizontal position at 70° C. for 20 minutes. The felt was mounted on double sided tape and slit into ⅕" ribbons. The ribbons were mounted on the distal side of a 6"×3 1.4" polystyrene plastic piece and the assembly was slit into ⅕" test strips.

Test strip performance was evaluated as follows. Aliquots of tap water with an alkalinity of 80 ppm were adjusted with dilute 0.24M HCl, or 0.24M NaOH to pH values of 6.4, 6.8, 7.2, 7.8 and 8.4, respectively. Test strips were evaluated in each of the solutions and compared to the results obtained using commercially available, state of the art pH test strips over a pH range of 6.4 to 8.4 (ETS). Phenol Red is a pH indicator, which is used in state of the art test strips for the determination of pool water pH. Phenol red is known to have a color transition interval of pH 6.4 to 8.0 with a color change from yellow to orange to red to purple.

| Tap Water Solution pH | Color Developed With Troy 777 Test Strips | Color Developed With ETS pH Test Strips | Color Developed With Troy 134 Test Strips | Color Developed With Troy 143 Test Strips |
| --- | --- | --- | --- | --- |
| 6.4 | Yellow | Orange | Light Yellow | Yellow |
| 6.8 | Yellow-Orange | Orange-Red | Light Yellow-Orange | Yellow-Orange |
| 7.2 | Orange | Darker Orange-Red | Light Orange | Orange |
| 7.8 | Red | Reddish Orange | Light Red | Red |
| 8.4 | Darker Reddish Purple | Slightly Darker Reddish Orange | Slightly Darker Red | Reddish Purple |

As can be seen from the results in the table, the test strips made with Troy 777 felt gave a more expanded color transition in the samples than the commercially available pH test strips. The Troy 143 test strips gave results almost as good as the Troy 777 test strips. The Troy 134 test strips gave good distinction at each pH level, even though the colors were lighter than that obtained with 777 and 143. The color range with the Troy 134 was still greater than that obtained with the commercially available test strips.

EXAMPLE 8

This example describes development of a free chlorine test strip using Troy 777 felt. The impregnating solution is as follows:

| Component | Amount |
| --- | --- |
| SD-30 Ethanol | 25 mL |
| 0.1% Syringaldazine in SD-30 Ethanol | 25 mL |
| 1.0% Aerosol or Surfactant in SD-30 ethanol | 0.75 mL |
| Distilled Water | 44.4 mL |
| 0.25 M Phosphate Buffer, pH 6.6 | 5 mL |
| 5.0% Gantrez AN 169 Polymer in distilled water | 0.625 mL |
| 5.0% PVP/VA-S630 Polymer in distilled water | 0.625 mL |

Figure 2:
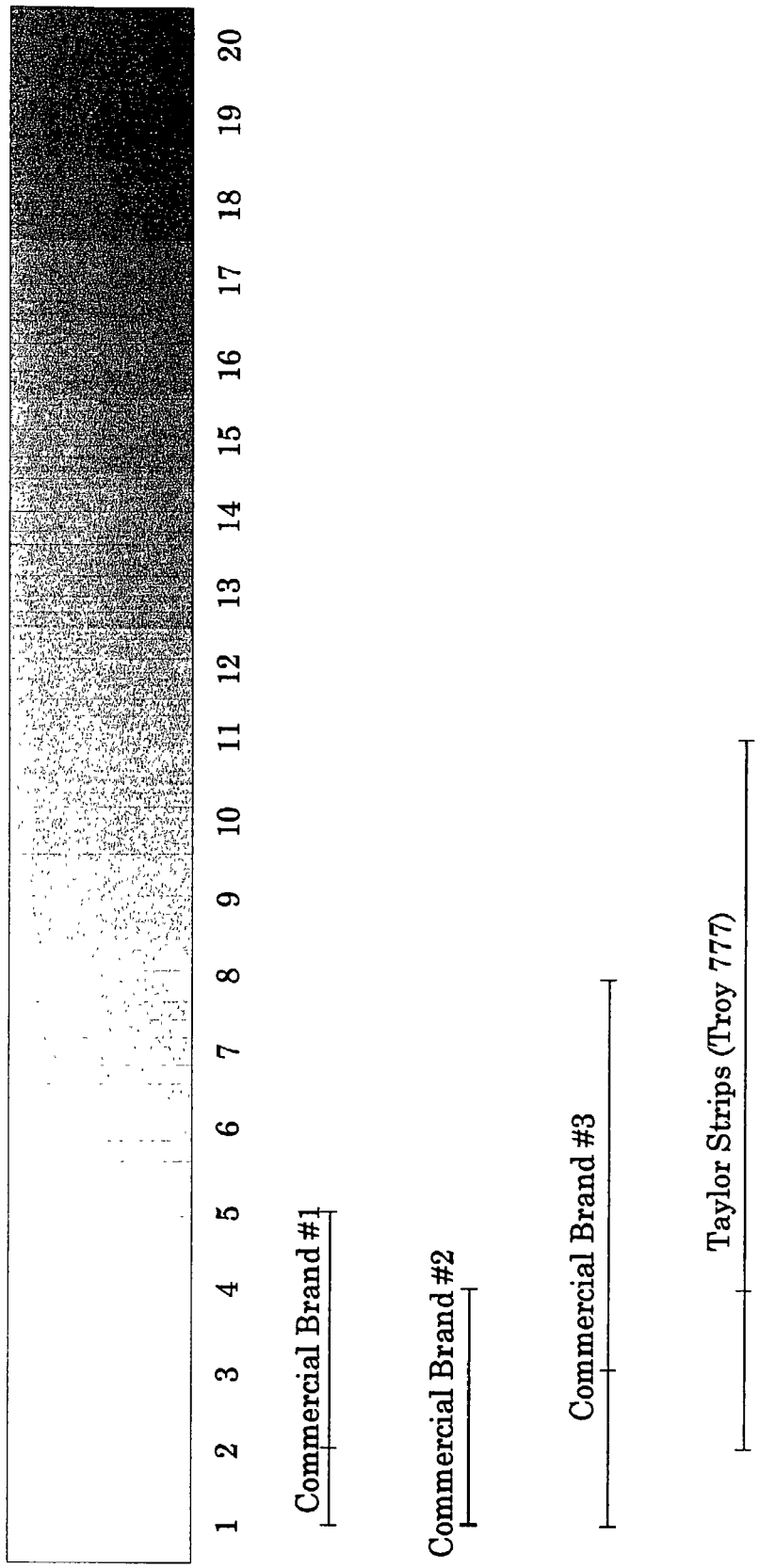
FIG. 2 depicts the range of color developed by free chlorine test strips.

Troy 777 felt was impregnated, and excess liquid was removed by blotting between paper towels. The material was dried at 90° C. for 10 minutes. Test strips were constructed by attaching double-sided adhesive to the felt and slitting into 5-mm wide ribbons. The ribbons were assembled to white plastic support and slit into 5-mm wide strips. The strips were tested in standard solutions of free chlorine at levels of 0, 0.5, 1.0 and 2.0 parts per million. State of the art commercially available free chlorine tests strips gave a color barely distinguishable between 0.0 and 1.0 parts per million, and only gave a color easily distinguishable between 0.0 and 2.0 parts per million. Strips prepared with the felt material easily distinguished between 0.0 and 1.0 parts per million. Further, the felt strips distinguished between 0.0 and 0.5 parts per million, thus showing greater sensitivity. The results shown in FIG. 2 clearly show that strips constructed with a felt matrix produce darker, more intense colors at a lower level than state-of-the-art commercially available test strips. The colors in FIG. 2 represent the possible range of colors, in 20 increments, obtained with Syringaldazine solutions over a chlorine range of 1 to 10 parts per million.

EXAMPLE 9

This example describes further test strips for free chlorine using another felt material.

First Dip 0.1 m Citrate-Phosphate Buffer, pH 6.0

Second Dip 0.25% Vanilin azine and 0.2% Syringaldazine in isopropyl alcohol/acetone, 1:1

10.0% Aerosol OT-100 in acetone

Durafelt 7251 felt was impregnated as described in the prior examples. The test strips were tested with 0.0, 0.4, 0.8 and 1.6 ppm free chlorine standards. The test strips easily distinguished between all levels of chlorine and particularly distinguished 0.0 from 0.4 ppm free chlorine. This test gave darker colors than state of the art free chlorine test strips.

EXAMPLE 10

Free chlorine test strips were prepared from Mead 469 filter paper, S&S 740E filter paper, Airformed Composites type STD230TF1, Troy 777 Felt and type A5 felt from the Felter's Group. All matrices were impregnated with the solution below:

| | |
| --- | --- |
| 0.1% Syringaldazine in SD-30 | 25 ml |
| 1% Aerosol OT in SD-30 | 0.75 ml |
| SD-30 | 25 ml |
| 0.25 M Phosphate Buffer | 5.0 ml |
| 5% PVP/VA S630 in Distilled Water | 0.625 ml |
| 5% Gantrez AN 169 in Distilled Water | 0.625 ml |
| Distilled Water | 44.4 ml |

Materials were dried at 90° C. for 15 minutes, then strips were prepared per as described supra. Reactivity was evaluated in free chlorine solutions at levels of 0, 1, 2, 3, 5 and 10 ppm. A color scale representing the colors developed by syringaldazine when reacted with chlorine was prepared in a series of 20 increments and numbered sequentially.

The reactivity, as shown in the table below, shows that felts and other highly bibulous matrices such as Airformed Composites type STD230TF1, produce much more sensitive test strips.

| Color Response of Chlorine Dip In Various Matrices Chlorine Levels | | | | | | |
|---|---|---|---|---|---|---|
| Matrix | 0 ppm | 1 ppm | 2 ppm | 3 ppm | 5 ppm | 10 ppm |
| Mead 469 | 1 | 1 | 1 | 3 | 2 | 20 |
| S & S 740E | 1 | 1 | 2 | 4 | 4 | 20 |
| Troy 777 | 1 | 9 | 12 | 18 | 19 | 20 |
| Felt A5 | 1 | 8 | 11 | 12 | 14 | 17 |
| Airformed Composites | 1 | 5 | 6 | 13 | 16 | 20 |

EXAMPLE 11

This example describes the use of felt matrices in water hardness test strips. An impregnation solution was prepared using:

| | |
|---|---|
| Buffer, pH 6.6 | 22.5 ml |
| 2% EDTA Solution in Distilled Water | 17.0 ml |
| 1% Hydroxynaphthol Blue in Distilled Water | 44.0 ml |
| Distilled Water | 12.5 ml |
| 5% Surfactant in Methanol | 1.0 ml |
| 5% Surfactant in Methanol | 1.0 ml |

Figure 3:
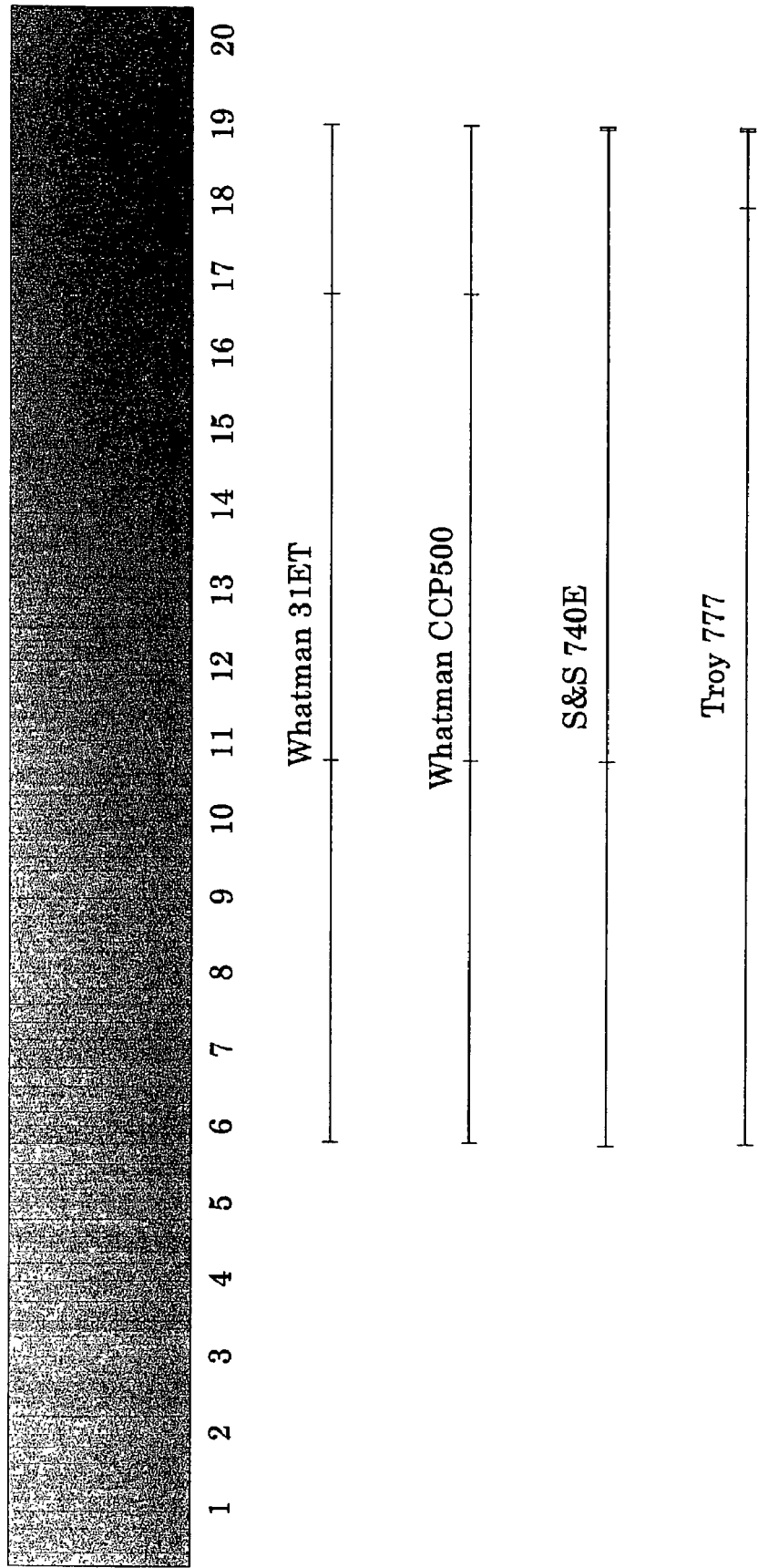
FIG. 3 depicts the range of colors developed by water hardness test strips.
Figure 4:
FIG. 4 depicts a matrix material containing reagent and an optional scrim, in accordance with the invention.

For comparison purposes, test strips were prepared from Whatman 31ET, Schleicher & Schuell 740E and Whatman CCP500 filter papers and Troy 777 felt. The strips were tested in aqueous solutions at levels of 0, 50, 100 and 200 ppm calcium carbonate hardness. The test strips prepared from the felt matrix showed more test sensitivity than any of the paper matrices. Results of this evaluation are shown in FIG. 3.

EXAMPLE 12

A protein test was prepared from the dip solution given below. Troy 777 felt was compared to Whatman 3 MM filter paper. Test strips were constructed as described, supra. A reagant dip solution was prepared according to the formula below. Citrate buffer was prepared by dissolving 12.5 g each of sodium citrate and citric acid in 100 ml D.I. water.

| Dip Solution | |
|---|---|
| Citrate Buffer | 50 ml |
| 1% Tetrabromophenolphthalein ethyl ester, potassium salt in D.I. Water | 25 ml |
| 0.1% FD&C Yellow #5 in D.I. Water | 5.0 ml |
| 5% Aerosol OT-100 in Methanol | 5.0 ml |

2"×6" pieces of Troy 777 felt were impregnated with the above solution, the excess liquid was removed by blotting between paper towels and dried in the horizontal position at 90° C. for 20 minutes. 2"×6" pieces of Whatman 3 MM paper were also impregnated with the dip solution, was removed by passing over a stirring rod, and they were then dried for 10 minutes at 90° C. Test strips were constructed as in the prior examples. Test strips were wing immersion in solutions of bovine serum albumin at 0, 10, 25, 50, 100, 200, 400 and 1000 mg/100 ml in distilled water.

| Protein Test Solution Concentration in mg/ml | Color Developed With Troy 777 Test Strips | Color Development With Whatman 3 MM Test Strips |
|---|---|---|
| 0 | Yellow | Pale Yellow |
| 10 | Slightly Dark Yellow | Pale Yellow |
| 25 | Greenish Yellow | Pale Yellow (very slightly different) |
| 50 | Light Green | Very Light Greenish Yellow |
| 100 | Slightly Darker Green | Light Green Yellow |
| 200 | Light Blue Green | Light Green Yellow |
| 400 | Blue Green | Pale Green |
| 1000 | Darker Blue Green | Light Green |

As can be seen from the results in the table, the test strips made with Troy 777 felt gave a much expanded color transition over the range of solutions tested then the 3 MM test strips. The colors of the felt strips were darker at each level, thus allowing easier distinction and increased sensitivity.

EXAMPLE 13

An iron test was prepared from the dip solution given below. Felt (STD230TF1 from Airformed Composites) was compared to Whatman 3 MM filter paper. Test strips were constructed as described, supra. A reagent dip solution was prepared from iron test reagents available from Taylor Technologies, Inc., Sparks, Md.

| Dip Solution | |
|---|---|
| 15 ml of R-0851 Iron Reagent #1 | 15 ml |
| 15 ml of R-0851 Iron Reagent #1 | 15 ml |

2"×6" pieces of the felt were impregnated with the above dip solution, the excess liquid was removed by blotting between paper towels and dried in the horizontal position at 90° C. for 20 minutes. 2"×6" pieces of Whatman 3 mm paper were also impregnated with the dip solution, and excess solution removed by pressing a stirring rod across it, and then dried for 10 minutes at 90° C. Test strips were constructed as above. Test strips were compared in solutions of iron at 0, 1, 5 and 10 ppm iron prepared by dilution of a 1,000 ppm standard solution in distilled water.

| Iron Concentration ppm | Color Developed With Airformed Composites Test Strips | Color Developed With Whatman 3 MM Test Strips |
|---|---|---|
| 0 | Light Grey | Very Light Grey |
| 1 | Light Blue | Pale Blue |
| 5 | Blue | Light Blue |
| 10 | Dark Blue | Slightly Darker Light Blue |

As can be seen from the results in the table, the test strips made with Airformed Composites felt gave a much expanded color transition over the range of solutions tested than the 3 MM test strips. The colors of the felt test strips were much darker at each level, thus allowing easier distinction and increased sensitivity.

EXAMPLE 14

An Additional iron test strip was prepared from the dip solution provided supra. Rayon felt from Buffalo Felt Products Corporation was compared to Whatman 3 MM filter paper. The reagent dip solution used was a commercially available material. 2"×6" pieces of the felt were impregnated with the dip solution, and excess was removed by blotting between paper towels and drying for 10 minutes at 90° C. 2"×6" piece of Whatman 3 MM paper was also impregnated with the dip solution, excess solution removed with a stirring rod and dried for 10 minutes at 90° C. Test strips were constructed as above and were tested in solutions of iron at 0, 1 and 10 ppm iron prepared by dilution of 1,000 ppm standard solution in distilled water.

| Iron Concentration ppm | Color Developed With Buffalo Felt Products Test Strips | Whatman 3 MM Test Strips |
|---|---|---|
| 0 | White | White |
| 1 | Pale Orange | White |
| 10 | Dark Orange | Pale Orange |

As can be seen from the results in the table, the test strips made with rayon felt gave much expanded color transition over the range of solutions tested than the 3 MM test strips. The colors of the felt test strips were much darker at each level, thus allowing easier distinction and increased sensitivity.

EXAMPLE 15

The materials tested for uptake ratios, supra, were then examined to determine their void volume, using the formula given, supra. The values are presented below:

| Material | Void Volume |
|---|---|
| *Non-Paper Materials* | |
| Aetna-PE9-125 | 93% |
| Buffalo Felt-PE-16-P | 75% |
| Buffalo Felt-Rayon | 93% |
| Felters-A5/000-100-8 | 92% |
| Foss-1AA680 | 93% |
| Troy-1-1915 | 89% |
| Troy-777 | 93% |
| *Paper* | |
| Ahlstrom-204 | 73% |
| Ahlstrom-205 | 81% |
| Ahlstrom-222 | 75% |
| Mead-74401 | 82% |
| S&S-740E | 78% |
| Whatman-CCP500 | 74% |
| Whatman-31 ET | 75% |
| Whatman-54 | 69% |

The foregoing disclosure sets forth various aspects of the invention, which relates to a test carrier useful in determining presence or amount of an analyte in a liquid sample. The test carrier comprises a matrix material which has a void volume of at least 80%, and more preferably more than this, as described supra. Such matrices can typically hold at least six times their own weight in liquid, more preferably about 6-25 times their weight in liquid, more preferably 6-20 times their weight in liquid, and most preferably 8-18 times their weight in liquid. The materials used to prepare the matrices can be chosen from any of the categories of materials used in the art, such as fleeces, felts, woven materials, non-woven materials, natural and synthetic materials, etc. Felts and fleeces, especially polyester fiber containing materials, are especially preferred. It must also be recognized that materials which, when untreated do not possess the ability to imbibe the amounts of liquid recited herein can be treated with agents, such as surfactants, to improve their ability to imbibe liquids. Methods and reagents for effecting these changes in properties are well known to the skilled artisan, and need not be reiterated herein. In additional embodiments, matrix materials in accordance with the invention comprise materials which possess a high open percent area on their surfaces, thereby imbibing liquid effectively.

It is useful to attach the test carriers of the invention to solid, inert materials, such as plastic or other inert materials, to prepare dip sticks, or other user friendly apparatus. In an especially preferred embodiment, the apparatus of the invention comprises a plurality of test carriers, each of which contains reagents for determining an analyte in a liquid sample. The plurality of carriers are all attached to a single, solid support means, as described supra, so that a plurality of analytes can be determined in a sample. "Plurality" as used herein, means at least two matrices.

A further feature of the invention is a kit for use in determining presence or amount of an analyte or analytes. Such kits include the apparatus described herein and, in addition, a reference for comparing any signal generated on the test matrices to standards, such as a color or intensity of color. In one embodiment, the test kit can be designed such that the apparatus are enclosed within a sealed, but openable container, with the reference material affixed permanently to the container. In another embodiment, the reference guide can be presented as an enclosure, and placed inside the container with the apparatus.

The test matrices are used, essentially, by dipping them into a liquid sample, and permitting analyte contained therein to react with a reagent or reagent system present in the matrix. The liquid sample may be, e.g., pool water, or water from any natural body of water, such as a lake, pond, river, stream, ocean, etc. "Run-off" water can be used as a sample, as can waste water, industrial water used for cooling, and so forth. Other liquids can be tested, such as biological fluids including blood, urine, sweat, cerebrospinal fluid, and so forth. Liquid foods stuffs such as juices, dairy products, and so forth can also be assayed to determine nutrient content, purity, and so forth.

Other features of the invention will be clear to the skilled artisan and need not be set forth here.

We claim:

1. A test carrier useful in determining presence or amount of an analyte present in a liquid sample, consisting essentially of a matrix material (i) having a void volume of at least about 80%, or (ii) capable of absorbing from about six to about twenty times its weight in liquid, wherein said matrix material contains a reagent which reacts with said analyte, said reagent comprising an indicator molecule which provides a detectable color signal in said matrix material in the presence of said analyte to indicate presence or amount of said analyte.

2. The test carrier of claim 1, wherein said matrix material has a void volume of at least about 85%.

3. The test carrier of claim 1, wherein said matrix material has a void volume of at least about 93% to about 97%.

4. The test carrier of claim 1, wherein said matrix material comprises a fleece.

5. The test carrier of claim 1, wherein said matrix material comprises a felt.

6. The test carrier of claim 5, wherein said felt is a polyester felt.

7. The test carrier of claim 1, wherein said matrix material comprises natural fiber material.

8. The test carrier of claim 1, wherein said matrix material comprises synthetic fiber material.

9. The test carrier of claim 1, wherein said matrix material comprises a woven material.

10. The test carrier of claim 1, wherein said matrix material comprises a non-woven material.

11. The test carrier of claim 1, wherein said matrix material is capable of absorbing from about eight to about eighteen times its weight of a liquid.

12. The test carrier of claim 1, wherein said reagent comprises a pH determination reagent system.

13. The test cater of claim 1, wherein said reagent comprises a free chlorine determination reagent system.

14. The test carrier of claim 1, wherein said reagent comprises a total chlorine determination reagent system.

15. The test cater of claim 1, wherein said reagent comprises a protein determination reagent system.

16. The test carrier of claim 1, wherein said reagent comprises an iron determination reagent system.

17. The test carrier of claim 1, wherein said reagent comprises a color enhancer.

18. The test carrier of claim 17, wherein said color enhancer is a glass bead, or diatormaceous earth.

19. An apparatus useful in determining presence or amount of an analyte present in a liquid sample consisting of the test carrier of claim 1 affixed to a solid support material.

20. A test kit useful in determining presence or amount of an analyte in a liquid sample, comprising the apparatus of claim 19, and a reference guide, which correlates the level of a detectable signal formed by said reagent with the presence or amount of said analyte.

* * * * *